(12) United States Patent
Martin et al.

(10) Patent No.: US 8,252,844 B2
(45) Date of Patent: Aug. 28, 2012

(54) METHOD OF STABILIZING AN ALDEHYDE

(75) Inventors: Antonietta Pamela Martin, Roodepoort (ZA); Mary G Skelly, Dublin (IE)

(73) Assignee: Microbide Limited, Dublin (IE)

( * ) Notice: Subject to any disclaimer, the term of this patent is extended or adjusted under 35 U.S.C. 154(b) by 67 days.

(21) Appl. No.: 12/594,637

(22) PCT Filed: Apr. 4, 2008

(86) PCT No.: PCT/ZA2008/000028
§ 371 (c)(1), (2), (4) Date: Apr. 1, 2010

(87) PCT Pub. No.: WO2008/134778
PCT Pub. Date: Nov. 6, 2008

(65) Prior Publication Data
US 2010/0190863 A1    Jul. 29, 2010

(30) Foreign Application Priority Data

Apr. 5, 2007 (ZA) .................................. 2007/03179

(51) Int. Cl.
*A01N 35/02* (2006.01)
*C09K 3/00* (2006.01)
*A01P 15/00* (2006.01)

(52) U.S. Cl. .......... 514/693; 514/696; 514/698; 252/29; 252/182

(58) Field of Classification Search .................. 514/693, 514/696, 698; 252/182.29
See application file for complete search history.

(56) References Cited

U.S. PATENT DOCUMENTS 4,880,602 A * 11/1989 Al-Sioufi ........................ 422/28
5,674,829 A * 10/1997 Martin .......................... 510/383
2004/0242702 A1* 12/2004 Martin .......................... 514/693

FOREIGN PATENT DOCUMENTS

EP    0867115 A2 *  9/1998

* cited by examiner

*Primary Examiner* — Sikarl Witherspoon
(74) *Attorney, Agent, or Firm* — Young & Thompson (57) ABSTRACT

A method of manufacturing a stable aldehyde-surfactant complex solution wherein at least one aldehyde is added to a surfactant in a first aliquot of water, at a temperature of between 40° C. to 50° C., the aldehyde is allowed to interact with the surfactant or detergent, in a complexing reaction, for at least 15 minutes whilst maintaining the temperature between 40° C. to 50° C. to produce an aldehyde-surfactant complex solution, and a second aliquot of water is added after at least 15 minutes to cool the aldehyde-surfactant complex solution to below 40° C. to stop the complexing reaction.

15 Claims, 4 Drawing Sheets

METHOD OF STABILIZING AN ALDEHYDE

BACKGROUND OF THE INVENTION

This invention relates generally to a stable aqueous aldehyde solution or mixtures of aldehyde solutions.

Aldehydes are widely used in many industrial processes. Importantly, due to the ability of an aldehyde functional group of an aldehyde molecule to react with free amine groups of, for example, a cell membrane of a microorganism, the aldehyde demonstrates a biocidal effect by disrupting and ultimately killing the microorganism.

Aldehydes are commonly used as preservatives, sanitizers, disinfectants and sporocidal agents.

However aldehydes (with the exception of formaldehyde and aldehydes with carbon chain lengths of 2 to 4 carbon atoms) have a tendency, especially at low concentrations, to adopt a cyclic molecular configuration which results in the aldehyde molecule losing its biocidal efficacy. Furthermore, aldehydes (including formaldehyde and aldehydes with carbon chain lengths of 2 to 4 carbon atoms) when in a monomeric form, which is prevalent at low concentrations, have a tendency to diffuse into the atmosphere causing a health hazard as potent dermal and respiratory irritants.

Aldehydes at relatively higher concentrations, left over a period of time, will polymerize with other aldehyde molecules, a process which accelerates at temperatures greater than 50° C. (and at less than 4° C. for aldehydes that have chain lengths of less than 5 carbon atoms). Once again this will result in a loss of the biocidal effect.

It is known in the art to take a product containing an aldehyde solution and, before use, to dilute it. In doing so the tendency of the aldehyde molecule to polymerize is reduced. Raising the pH subsequently activates the aldehyde solution. The activation increases the reactivity of the aldehyde functional groups with the amine groups and the associated biocidal effect upon cell membranes. However the stability of the aldehyde solution is compromised in so doing to the extent that the solution is only stable for several days.

There are a number of problems associated with the use of an aldehyde solution as a biocidal product. Not only does a user have to dilute the product prior to use but also activate it. The resultant diluted and activated product is corrosive, due to the high pH, and unstable beyond a month.

The invention at least partially addresses the aforementioned problems.

SUMMARY OF INVENTION

The invention provides a stable aqueous aldehyde solution that includes:
(a) an aldehyde comprising at least one of the following: a monoaldehyde (Diagram 1), a cyclic aldehyde (Diagram 2) and a dialdehyde (Diagram2) and a monoaldehyde or a cyclic aldehyde in a 0.001% to 25% m/v concentration:

Diagram 1

Diagram 2

Diagram 3 and wherein:
$R$ = hydrogen, a straight hydrocarbon chain between 1 and 12 carbon atoms in length, or a branded hydrocarbon chain between 2 and 12 carbon atoms in length;
— $R_1$ = a hydrocarbon chain between 2 and 12 carbon atoms in length; and
— $R_3$ = a cyclic hydrocarbon having 5 or 6 carbon atoms.
(b) a surfactant or detergent chosen from any one of the following: an alcohol ethoxylate surfactant, a nonylphenol surfactant, sulphonic acid, sodium lauryl ethyl sulphate, sodium lauryl sulphate, a twin chain quaternary ammonium compound and cocopropyldiamide (CPAD);
(c) a sufficient amount of a pH modifier to bring the pH of the solution to within a 6.0 to 8.5 range; and
(d) a buffer comprising at least one of the following: calcium acetate, magnesium acetate, sodium acetate, sodium acetate tri-hydrate, potassium acetate, lithium acetate, propylene glycol, hexalene glycol, sodium phosphate, sodium tri-phosphate, potassium phosphate, lithium phosphate, zinc perchlorate, zinc sulphate, cupric chlorate and cupric sulphate.

"Stable", in the context of the invention, refers to an aqueous aldehyde solution capable of being stored for a period of at least six months without the aldehyde molecules polymerizing or the pH dropping below 5.

The stable aqueous aldehyde solution may include any of the following aldehydes: formaldehyde, acetaldehyde, proprionaldehyde, butraldehyde, pentanaldehyde, hexanaldehyde, heptanaldehyde, octanaldehyde, nonanaldehyde, glutaraldehyde, succinaldehyde, Glyoxal™, 2-ethyl hexanal, isovaleraldehyde, chloraldehyde hydrate, furfuraldehyde, paraformaldehyde.

Preferably, the stable aqueous aldehyde solution includes any of the following aldehyde mixtures: glutaraldehyde and Glyoxal™ (ethane dialdehyde); Glyoxal™ chloraldehyde trihydrate; acetaldehyde and Glyoxal™; paraformaldehyde and glutaraldehyde, glutaraldehyde and succinaldehyde and Glyoxal™ and succinaldehyde.

The stable aqueous aldehyde solution preferably includes the surfactant or detergent in a 0.1% to 25% m/v concentration.

The surfactant is preferably a non-ionic surfactant such as an alcohol ethoxylate surfactant.

The alcohol ethoxylate surfactant may include 3 to 9 ethoxylate groups depending on the composition of the stable aqueous aldehyde solution and the foaming properties required for a specific application of the stable aqueous aldehyde solution.

The buffer is preferably a mixture of sodium acetate trihydrate and potassium acetate.

To maintain the pH of the stable aqueous aldehyde solution at least at 5 or above for at least 6 months, the buffer is preferably included in the solution in a concentration of at least 0.05% m/v.

The pH modifier may be any one or more of the following compounds: potassium hydroxide, sodium hydroxide, sodium phosphate and sodium bicarbonate.

The pH modifier is preferably potassium hydroxide in a one molar solution.

The pH of the stable aqueous aldehyde solution may be maintained, at the time of manufacture, within a 7.0 to 8.5 range.

A twin chain quaternary ammonium compound with sterically hindered ammonium groups may be added to the stable aqueous aldehyde solution for its fungicidal and foaming properties.

To enhance the biocidal efficacy of the stable aqueous aldehyde solution one or more of the following trace elements may be added to the solution: calcium, magnesium, zinc, copper, titanium, iron, silver, sodium and gold.

Sodium nitrite may be added to the stable aqueous aldehyde solution in a concentration exceeding 0.005% m/v for its anti-corrosive properties.

Copper may be added to the stable aqueous aldehyde solution e.g. as cupric chlorate or cupric sulphate.

Zinc may be added to the stable aqueous aldehyde solution e.g. as zinc perchlorate, zinc chloride or zinc sulphate.

The stable aqueous aldehyde solution may be diluted either with distilled or potable water, an alcohol or a solvent to produce a biocidal dispersant with a greater biocidal efficacy at lower temperatures than the stable aqueous aldehyde solution in an undiluted state.

The invention also provides a method of manufacturing a stable aldehyde-surfactant complex solution wherein at least one aldehyde is added to a surfactant in a first aliquot of water, at a temperature of between 40° C. to 50° C., the aldehyde is allowed to interact with the surfactant or detergent, in a complexing reaction, for at least 15 minutes whilst maintaining the temperature between 40° C. to 50° C. to produce an aldehyde surfactant complex solution, and a second aliquot of water is added after at least 15 minutes to cool the aldehyde-surfactant complex solution to below 40° C. to stop the complexing reaction.

The aldehyde may be a monoaldehyde (Diagram 1), dialdehyde (Diagram 2) or a cyclic aldehyde (Diagram 3) in a 0.001% to 25% m/v concentration:

R—CHO      Diagram 1

OHC—$R_1$—CHO      Diagram 2

$R_3$—CHO      Diagram 3 and wherein:
R=hydrogen or a straight hydrocarbon chain between 1 and 10 carbon atoms in length or a branded hydrocarbon chain between 2 and 12 carbon atoms in length;
—$R_1$=a hydrocarbon chain between 2 and 10 carbon atoms in length; and
—$R_3$=a cyclic hydrocarbon having 5 or 6 carbon atoms.

The surfactant may be at least one of the following; an alcohol ethoxylate surfactant, a nonylphenol surfactant, sulphonic acid, sodium lauryl ethyl sulphate, sodium lauryl sulphate, a twin chain quaternary ammonium compound and cocopropyldiamide (CPAD).

BRIEF DESCRIPTION OF THE DRAWINGS

The invention is further described by way of example with reference to the accompanying drawings in which.

DESCRIPTION OF PREFERRED EMBODIMENT

A stable aqueous aldehyde solution, according to the invention, is manufactured, in a concentrate solution (i.e. comprising aldehyde compounds in the range 2 to 10% m/v), by first adding a non-ionic surfactant i.e. alcohol ethoxylate (with 3, 7 or 9 ethoxylate groups), to water heated to a temperature between 40° and 50° C. followed by an aldehyde or an aldehyde mixture chosen from Table 1 (hereinafter referred to as "the aldehyde").

TABLE 1

| aldehyde | aldehyde mixture | Preferred surfactant |
|---|---|---|
| 1. | Glyoxal ™/glutaraldehyde | alcohol ethoxylate 7 |
| 2. Glyoxal ™ | | alcohol ethoxylate 9 |
| 3. | Glyoxal ™/chloraldehyde trihydrate | alcohol ethoxylate 9 |
| 4. succinaldehyde | | alcohol ethoxylate 7 |
| 5. | Glutaraldehyde/succinaldehyde | alcohol ethoxylate 7 |
| 6. | Glyoxal ™/succinaldehyde | alcohol ethoxylate 9 |
| 7. acetaldehyde | | alcohol ethoxylate 9 |
| 8. | acetaldehyde/Glyoxal ™ | alcohol ethoxylate 9 |
| 9. | glutaraldehyde/ paraformaldehyde | alcohol ethoxylate 9 |

The aldehyde is allowed to complex with the preferred alcohol ethoxylate (as indicated in Table 1 alongside the relevant aldehyde) for a period of between 15 and 30 minutes. This produces an aldehyde-surfactant solution, whilst maintaining the temperature of the body of water between 30° C. and 70° C. During this period of heating the aldehyde complexes with the alcohol ethoxylate substantially to completion (see FIGS. 2 and 3).

Following this period, a further amount of water, at a temperature of less than 25° C., is added to the aldehyde-surfactant complex solution to reduce the temperature of the solution to below 30° C. thereby to stop the complexing reaction of the alcohol ethoxylate with the aldehyde.

A pH modifier, such as potassium hydroxide, is then added in a sufficient quantity to adjust the pH of the succinaldehyde-surfactant complex solution to within 7.0 to 85 Potassium hydroxide is used in a one molar solution.

Finally a buffer mixture comprising sodium acetate trihydrate and potassium acetate is added to the aldehyde-surfactant complex solution to produce a stable aqueous aldehyde solution in the concentrate solution.

Sodium acetate trihydrate and potassium acetate each have a concentration in the buffer mixture of between 0.250 to 0.500 grams/liter. This concentrated solution is diluted when added to the aldehyde-surfactant complex solution to within the range 0.005% to 0.1% m/v.

The buffer mixture maintains the pH of the concentrate during the shelf life of the stable aqueous aldehyde solution, i.e. at least 6 months from manufacture, at least above pH 5.

The concentrate solution of the stable aqueous aldehyde solution includes the following contents in the following concentrations:

| | |
|---|---|
| (a) aldehyde | 0.01% to 25% m/v; |
| (b) alcohol ethoxylate | 0.1% to 25% m/v; and |
| (c) the buffer mixture | 0.05% to 0.1% m/v. |

To enhance the biocidal efficacy of the stable aqueous aldehyde solution, one or more of the following trace elements are added, in a concentration not exceeding 5 ppm, to the solution: calcium, magnesium, zinc, copper, titanium, iron, silver and gold.

To produce a biocidal product capable of application, by a variety of means, to a variety of surfaces, the concentrate solution of the stable aqueous aldehyde solution is diluted with potable water to produce a dispersant with aldehyde in a 0.001% to 8% m/v concentration.

The dispersant finds application as an additive to degreasing agents, detergents, thickeners, fragrances, colorants, skin conditioners and a variety of anti-microbial products. This list is exemplary and is by no means exhaustive.

On the other hand, the concentrate solution with aldehyde in a concentration in excess of 10% m/v is a favoured composition in which to transport the stable aqueous aldehyde solution.

An end user, on receipt of the concentrate solution, merely has to dilute the concentrate solution by a required dilution ratio for ready incorporation with other appropriate additives, to produce products such as anti-microbial hand soap, hand sanitizers, medical equipment disinfectants, dishwashing liquids, and laundry detergents. Once again, this list is exemplary and is by no means exhaustive.

The concentrate solution finds further application, incorporated with other mediums such as paints, resins etc, to provide a sustained release of the biocidal efficacy.

It is believed that the dispersant and the concentrate solution, in the variety of applications exemplified above, have lower volatility, lower toxicity and corrosive properties, greater stability and biocidal efficacy at room temperatures relatively to an aldehyde (e.g. acetaldehyde and/or Glyoxal™) that has not been subjected to the method of the invention (i.e. at least not bound to a surfactant in a complex configuration), and which is used in comparative applications (see Table 2, Table 3 and Table 4).

The stable aqueous aldehyde solution, like an uncomplexed aldehyde, is incompatible with certain unhindered nitrogen containing chemicals such as triethalamines and cocoamides. This incompatability needs to be kept in consideration when formulating with any aldehyde biocide.

EXAMPLE 1

Proof of Complexing

Figure 1:
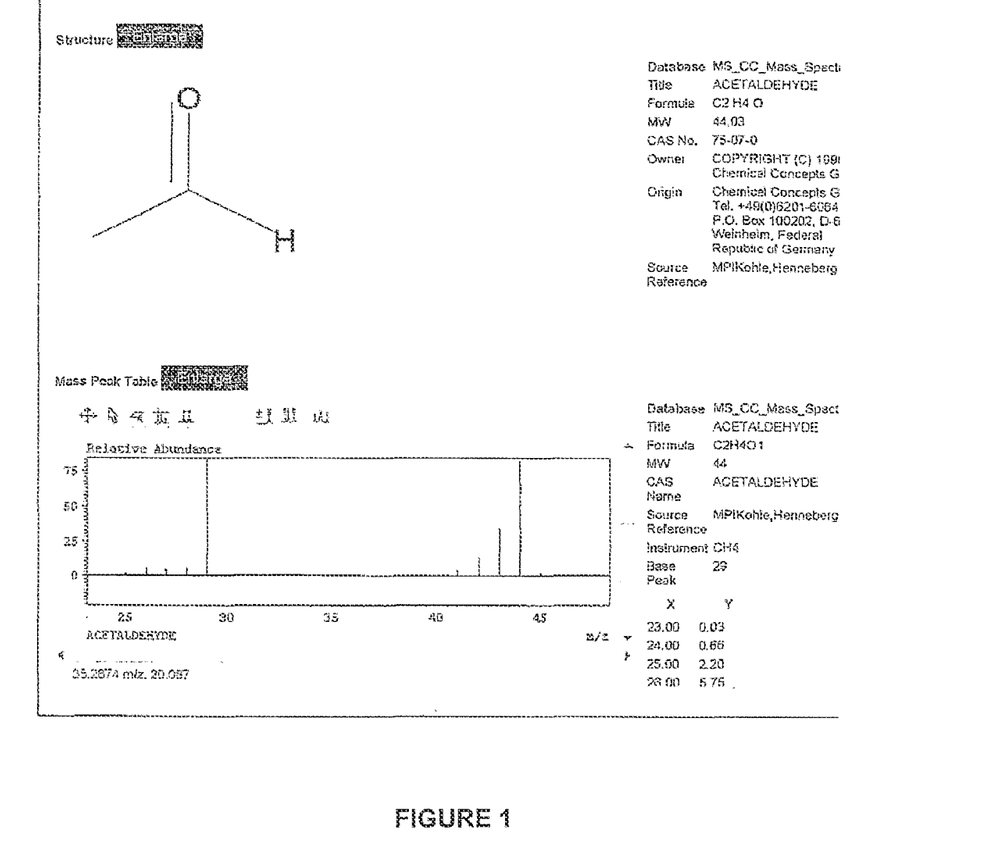
FIG. 1 illustrates a commercially available mass spectroscopy scan of acetaldehyde.
Figure 2A:
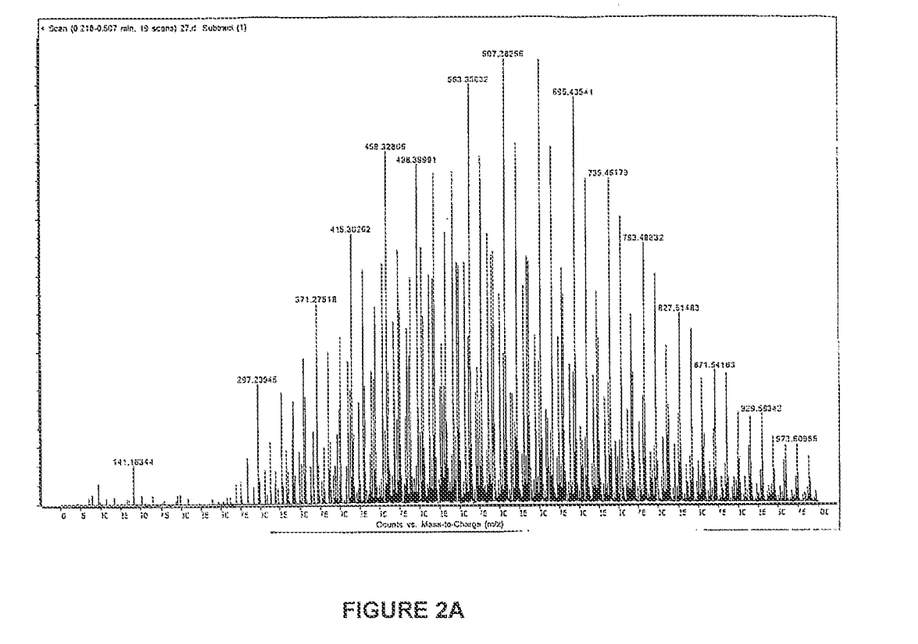
FIG. 2A illustrates a mass spectroscopy scan of acetaldehyde treated in accordance with the invention.
Figure 2B:
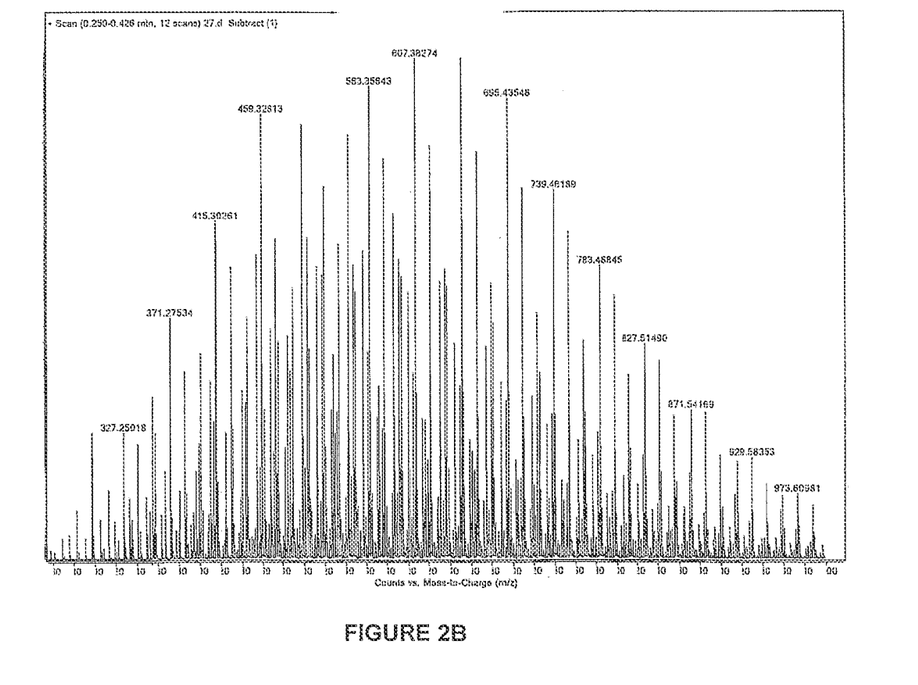
FIG. 2B illustrates an expanded portion of the mass spectroscopy scan of FIG. 2A.

To demonstrate complexing of the aldehyde with the surfactant a comparison is made between FIG. 1 and FIG. 2.

From FIG. 2 it is evident that there are no free acetaldehyde spectra between 0 to 100 mass to charge (m/z) where acetaldehyde indicative peaks would appear (see FIG. 1) if "free" aldehyde was present.

Figure 3A:
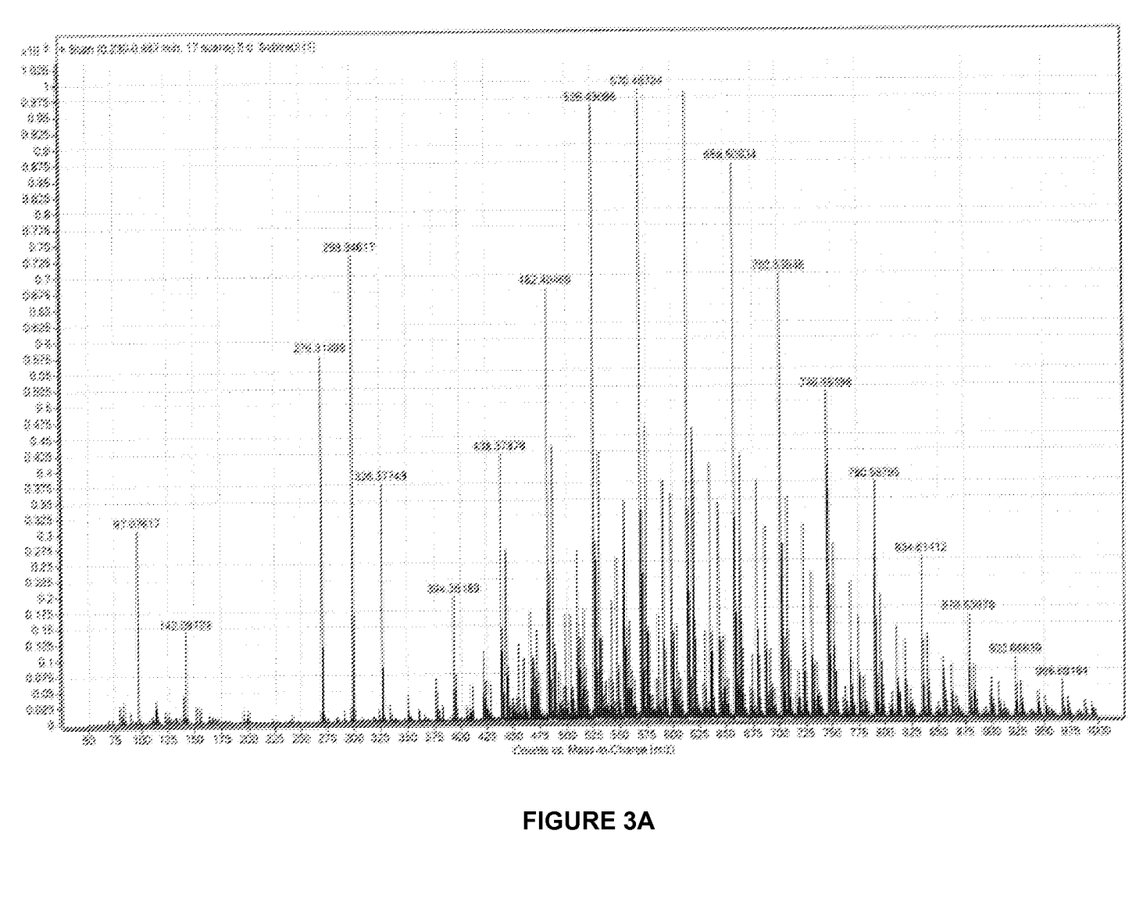
FIG. 3A illustrates a mass spectroscopy scan of untreated acetaldehyde and a surfactant.
Figure 3B:
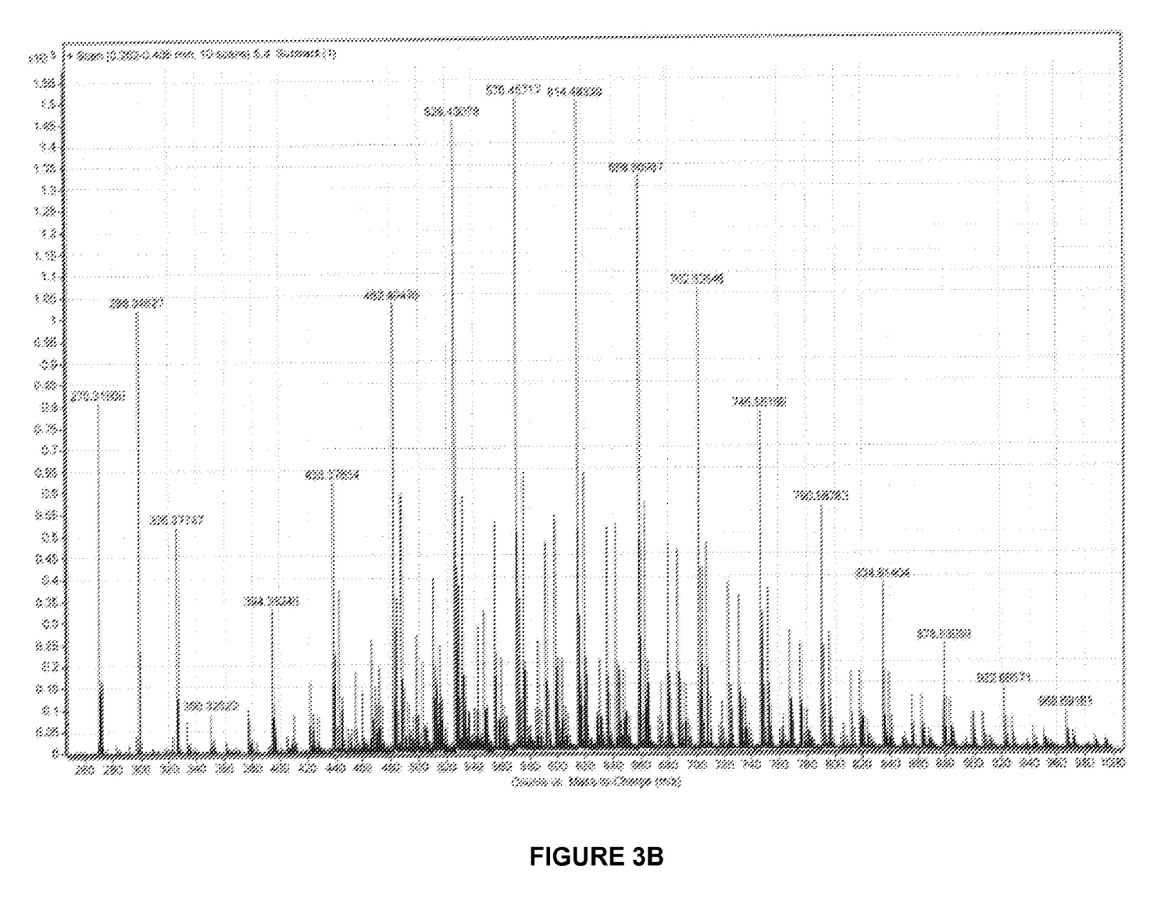
FIG. 3B illustrates an expanded portion of the mass spectroscopy scan of FIG. 3A.

FIG. 3 exhibits the separate mass spectra of the surfactant and the aldehyde used in FIG. 2, but uncomplexed with each other. By comparing FIG. 2 with FIG. 3 it can be seen that the spectra of FIG. 2 have shifted to the right with respect to the spectra of FIG. 3, indicating the complexing of the aldehyde with the surfactant.

The sample of FIG. 2 was produced by adding 50 ml acetaldehyde (10% m/v) to 450 ml of a "premix" solution (2.51 bacterial filtered water, 0.9% m/v alcohol ethoxylate 7, 13.7 g potassium acetate, 13.7 g sodium acetate trihydrate) and heated to 30° C. for 15 minutes.

The sample of FIG. 3 was a sample of acetaldehyde (99% m/v), mixed with an alcohol ethoxylate 7 surfactant without being subjected to the method of the invention.

The method, materials and equipment used in this example are as follows: Agilent 1299LC; Agilent 6210 Agilent 6210 time-of-flight (TOF) mass spectroscopy; LC: mobile phase: 50:50 H20:MeCN+0.1% formic acid; flow: 0.2 ml/min; injection volume: 10 micro-liter; samples were directly infused into the TOF; TOE: positive ionization; gas Temp 300° C.; drying gas 8 L/min; nebulizer 35 psig; Vcap 3500V; fragmenter 140V; skimmer 60V; ref masses: 118.086255 and 922.009798.

The TOF system is used in combination with a dual-nebulizer ESI source and an automated calibrant delivery system to continuously introduce low-level reference masses to achieve accurate mass assignment. For the analysis, the drying gas flow was set at 8 L/min, with gas temperature at 300° C. The nebulizer was set to 35 psig and capillary voltage was 3500V. A Fragmenter setting of 140V was used with skimmer 60V. The mass range was set to 100-3500 m/z with transients/scan equal to 10000. Internal reference mass correction was used.

Stability tests, as above, were repeated on samples of the aldehydes (1 to 21) indicated in the table below. The results showed the same complexing phenomena.

EXAMPLE 2

Biocidal Efficacy Tests

Tests were conducted using a South African Bureau of Standards (SABS) method (i.e. SABS1593), a Kelsey Sykes modified suspension test. The microorganism used in the test was *Bacillus subtilis* var *globi*. The results of the tests are tabulated below:

TABLE 2

| Aldehyde 1 | Aldehyde 2 (% m/v) | Surfactant | Suspension Contact time | Result |
|---|---|---|---|---|
| 1 glutaraldehyde 1.5% | Glyoxal ™ 8% | alcohol ethoxylate 7 | 2 hrs<br>4 hrs<br>8 hrs | PASS<br>PASS<br>PASS |
| 2 Glyoxal ™ 16% | | alcohol ethoxylate 9 | 2 hrs<br>4 hrs<br>8 hrs | PASS<br>PASS<br>PASS |
| 3 Glyoxal ™ 8% | chloraldehyde trihydrate 10% | alcohol ethoxylate 9 | 2 hrs<br>4 hrs<br>8 hrs | PASS<br>PASS<br>PASS |
| 4 succinaldehyde 3% | | alcohol ethoxylate 7 | 2 hrs<br>4 hrs<br>8 hrs | FAIL<br>PASS<br>PASS |
| 5 glutaraldehyde 1% | succinaldehyde 2% | alcohol ethoxylate 7 | 2 hrs<br>4 hrs<br>8 hrs | PASS<br>PASS<br>PASS |
| 6 Glyoxol ™ 8% | Succinaldehyde 1% | alcohol ethoxylate 9 | 2 hrs<br>4 hrs<br>8 hrs | PASS<br>PASS<br>PASS |
| 7 acetaldehyde 3% | | alcohol ethoxylate 9 | 2 hrs<br>4 hrs<br>8 hrs | PASS<br>PASS<br>PASS |
| 8 acetaldehyde 2% | Glyoxal ™ 8% | alcohol ethoxylate 9 | 2 hrs<br>4 hrs<br>8 hrs | BORDER PASS<br>PASS<br>PASS |
| 9 acetaldehyde 1% | paraformaldehyde 1% | alcohol ethoxylate 9 | 2 hrs<br>4 hrs<br>8 hrs | BORDER PASS<br>PASS<br>PASS |
| 10 Glyoxal ™ 10% | | alcohol ethoxylate 3 | 2 hrs<br>4 hrs<br>8 hrs | PASS<br>PASS<br>PASS |
| 11 furfuraldehyde 5% | | alcohol ethoxylate 3 | 2 hrs<br>4 hrs<br>8 hrs | BORDER PASS<br>PASS<br>PASS |
| 12 furfuraldehyde 5% | | alcohol ethoxylate 9 | 2 hrs<br>4 hrs<br>8 hrs | PASS<br>PASS<br>PASS |
| 13 glutaraldehyde 3% | | alcohol ethoxylate 3 | 2 hrs<br>4 hrs<br>8 hrs | FAIL<br>PASS<br>PASS |

TABLE 2-continued

| Aldehyde 1 | Aldehyde 2 (% m/v) | Surfactant | Suspension Contact time | Result |
|---|---|---|---|---|
| 14 2-ethyl hexanaldehyde 10% | | alcohol ethoxylate 3 | 2 hrs | FAIL |
| | | | 4 hrs | FAIL |
| | | | 8 hrs | PASS |
| 15 2-ethyl hexanaldehyde 10% | | alcohol ethoxylate 9 | 2 hrs | FAIL |
| | | | 4 hrs | PASS |
| | | | 8 hrs | PASS |
| 16 nonanaldehyde 15% | | alcohol ethoxylate 3 | 2 hrs | FAIL |
| | | | 4 hrs | PASS |
| | | | 8 hrs | PASS |
| 17 nonanaldehyde 15% | | alcohol ethoxylate 9 | 2 hrs | FAIL |
| | | | 4 hrs | PASS |
| | | | 8 hrs | PASS |
| 18 chloraldehyde hydrate 20% | | alcohol ethoxylate 3 | 2 hrs | FAIL |
| | | | 4 hrs | PASS |
| | | | 8 hrs | PASS |
| 19 chloraldehyde hydrate 20% | | alcohol ethoxylate 9 | 2 hrs | FAIL |
| | | | 4 hrs | PASS |
| | | | 8 hrs | PASS |
| 20 paraformaldehyde 3% | | alcohol ethoxylate 9 | 2 hrs | FAIL |
| | | | 4 hrs | PASS |
| | | | 8 hrs | PASS |
| 21 formaldehyde 10% | | alcohol ethoxylate 9 | 2 hrs | FAIL |
| | | | 4 hrs | PASS |
| | | | 8 hrs | PASS |

The same aldehydes as used above (i.e. 1 to 21) were re-subjected to the test, with the relevant surfactant added, but without pH adjustment and without the addition of a pH modifier and a buffer. All the aldehydes failed the 8 hour contact time with the exception of glutaraldehyde (sample 13) with a "borderline" pass.

As evident from the above the invention appears effective at improving the biocidal efficacy of aldehydes.

EXAMPLE 3

Stability Tests

TABLE 3

| Sample number | Description of sample (% m/v) | Start | 1 wk | 2 wk | 1 mth | 2 mth | 3 mth |
|---|---|---|---|---|---|---|---|
| | | 25° C. Temp pH % aldehyde m/v (% al) 40° C. (accelerated stability test) pH % al | 25° C. pH % al 40° C. pH % al | 25° C. pH % al 40° C. pH % al | 25° C. pH % al | 25° C. pH % al | 25° C. pH % al |
| 1 | Glyoxal 10% | 5.38 Slightly cloudy 10.65 | 5.37 10.58 5.25 | 5.36 10.62 5.15 | 5.37 10.61 | 5.33 | |
| 2 | 2-ethly hexanal 10% | 5.76 Milky top clear bottom mixed all milk 10.4 | 5.73 10.35 5.53 | 5.75 10.35 5.47 | 5.76 10.4 | 5.70 | |
| 3 | furfuraldehyde 10% | 6.91 Clear yellow top dark brown bottom Mixed all creamy brown 9.87 | 6.85 9.85 6.57 | 6.89 9.81 6.35 | 6.93 9.75 | 6.80 | |
| 4 | glutaraldehyde 10% | 5.3 Clear (Terg 3) 11.02 | 5.45 10.97 5.11 | 5.32 10.89 5.09 | 5.43 10.95 | 5.33 | |
| 5 | acetaldehyde 10% | 6.47 Clear 10.36 | 6.45 10.32 6.12 | 6.51 10.28 6.06 | 6.531 10.33 | 6.4 | |
| 6 | formaldehyde 10% | 7.09 Clear 9.98 | 7.12 9.97 6.85 | 7.17 9.84 6.73 | 7.20 9.99 | 6.90 | |
| 7 | butyraldehyde 10% | 5.22 Smells slight cloudy top bottom clear mixed all cloudy 10.05 | 5.3 10.1 5.04 | 5.28 10.02 5.02 | 5.36 10.00 | 5.20 | |
| 8 | nonanal 10% | 6.38 White top cloudy bottom mix milky 10.65 | 6.44 10.63 6.16 | 6.43 10.7 5.98 | 6.53 10.45 | 6.35 | |
| 9 | chloral hydrate 2% | 6.32 Slight cloudy 2.18 | 6.35 2.18 6.00 | 6.3 2.19 5.87 | 6.41 2.18 | 6.29 | |

TABLE 3-continued

| Sample number | Description of sample (% m/v) | Start | 1 wk | 2 wk | 1 mth | 2 mth | 3 mth |
|---|---|---|---|---|---|---|---|
| 10 | paraformaldehyde 10% | 7.43<br>Cloudy ppt<br>10.16 | 7.36<br>10.19<br>7.14 | 7.42<br>10.15<br>6.98 | 7.56<br>10.17 | 7.30 | |
| 11 | 3% Glyoxal + tergitol (Terg) 3 | 6.26<br>Clear oily ppt on top<br>2.98 | 6.28<br>2.97<br>6.00 | 6.3<br>3.01<br>5.86 | 6.32<br>2.99 | 6.15 | |
| 12 | 3% Glyoxal + Terg 9 | 6.33<br>Clear<br>3.02 | 6.32<br>2.97<br>5.99 | 6.33<br>2.98<br>5.74 | 6.34<br>3.00 | 6.19 | |
| 13 | 3% furfuraldehyde + Terg 3 | 7.32<br>Oily brown ppt top bottom cloudy<br>2.89 | 7.27<br>2.84<br>7.01 | 7.29<br>2.86<br>6.91 | 7.25<br>2.84 | 7.18 | |
| 14 | 3% furfuraldehyde + Terg 9 | 7.59<br>Clear yollow<br>2.79 | 7.55<br>2.81<br>7.27 | 7.56<br>2.80<br>7.02 | 7.51<br>2.78 | 7.41 | |
| 15 | 3% glutaraldehyde + Terg 3 | 6.47<br>Clear oily ppt on top<br>3.00 | 6.45<br>2.98<br>6.24 | 6.38<br>2.97<br>6.05 | 6.34<br>2.86 | 6.31 | |
| 16 | 3% 2-ethyl hexanal + Terg 3 | 6.20<br>Clear<br>2.99 | 6.15<br>2.86<br>6.01 | 6.10<br>2.76<br>5.91 | 6.08<br>2.89 | 6.11 | |
| 17 | 3% 2-ethyl hexanal + Terg 9 | 5.65<br>Cloudy<br>2.99 | 5.4<br>2.97<br>5.69 | 5.43<br>2.90<br>5.56 | 5.45<br>2.95 | 5.50 | |
| 18 | 3% nonanal + Terg 3 clear | 6.50<br>Clear oily top bottom clear mix cloudy<br>2.89 | 6.49<br>2.95<br>6.19 | 6.46<br>2.96<br>6.00 | 6.45<br>2.87 | 6.31 | |
| 19 | 3% nonanal + Terg 9 clear | 6.41<br>Milk top cloudy bottom mix milk<br>2.85 | 6.4<br>2.86<br>6.06 | 6.38<br>2.83<br>5.86 | 6.42<br>2.87 | 6.32 | |
| 20 | 3% of 2% chloral hydrate + Terg 3 | 6.64<br>Clear oily top bottom clear<br>0.1 | 6.65<br>0.12<br>6.17 | 6.55<br>0.11<br>5.99 | 6.7<br>0.12 | 6.35 | |
| 21 | 3% of 2% chloral hydrate + Terg 9 | 6.61<br>Clear<br>0.13 | 6.58<br>0.12<br>6.17 | 6.53<br>0.10<br>6.00 | 6.62<br>0.11 | 6.30 | |
| 22 | 3% sodium perborate tetra hydrate + Terg 9 | 11.01<br>Clear (gas) | 10.98<br>10.06 | 10.85<br>10.54 | 10.9 | 10.81 | |
| 23 | 3% paraformaldehyde + Terg 9 | 8.04<br>Clear slight smell<br>3.01 | 7.89<br>2.99<br>7.89 | 7.78<br>2.97<br>7.72 | 7.65<br>2.95 | 7.85 | |
| 24 | 3% acetaldehyde + Terg 9 | 8.09<br>Clear slight smell<br>3.01 | 7.97<br>2.99<br>7.82 | 7.86<br>2.98<br>7.73 | 7.78<br>3.00 | 7.90 | |
| 25 | 3% formaldehyde + Terg 9 | 7.82<br>Clear smell<br>3.1 | 7.79<br>3.06<br>7.46 | 7.63<br>2.99<br>7.36 | 7.55<br>3.00 | 7.60 | |

The tests conducted at 40° C. are accelerated stability tests i.e. a 2 week period at the elected temperature (40° C.) is equivalent to a 6 month "shelf-life" period at 25° C.

The aldehyde samples chosen for this test are merely exemplary of the vast number of possible aldehyde and mixed aldehyde permutations of the invention.

The three month results were not available at the time of filing.

EXAMPLE 4

Virucidal Efficacy Tests

The same aldehyde samples as used in Example 3 (i.e. 1 to 25) were tested for virucidal efficacy using a standard SABS method (SANS1288) which uses a bacteriophage with virus standard to represent enveloped and non-enveloped viruses Each of the samples passed the test.

The invention claimed is:
1. A stable aqueous aldehyde solution that includes:
(a) an aldehyde comprising at least one of the following: a monoaldehyde (Diagram 1), a dialdehyde (Diagram 2) and a cyclic aldehyde (Diagram 3) in a 0.001% to 25% m/v concentration:

Diagram 1

Diagram 2

Diagram 3 and wherein:

R = hydrogen, a straight hydrocarbon chain between 1 and 12 carbon atoms in length, or a branched hydrocarbon chain between 2 and 12 carbon atoms in length;

—$R_1$ = a hydrocarbon chain between 2 and 12 carbon atoms in length; and

—$R_3$ = a cyclic hydrocarbon having 5 or 6 carbon atoms, (b) a surfactant or detergent selected from the group consisting of: an alcohol ethoxylate surfactant, a nonylphenol surfactant, sodium lauryl ethyl sulphate, sodium lauryl sulphate, and cocopropyldiamide (CPAD);

(c) a sufficient amount of a pH modifier to bring the pH of the solution to within a 6.0 to 8.5 range; and (d) a buffer comprising sodium acetate or sodium acetate tri-hydrate and at least one component selected from the group consisting of: potassium acetate, calcium acetate, magnesium acetate, lithium acetate, propylene glycol, hexalene glycol, sodium phosphate, sodium tri-phosphate, potassium phosphate, lithium phosphate, zinc perchlorate, zinc sulphate, cupric chloride and cupric sulphate.

2. The stable aqueous aldehyde solution according to claim 1 wherein the aldehyde comprises at least one component selected from the group consisting of: formaldehyde, acetaldehyde, proprionaldehyde, butraldehyde, pentanaldehyde, hexanaldehyde, heptanaldehyde, octanaldehyde, nonanaldehyde, glutaraldehyde, succinaldehyde, ethane dialdehyde, 2-ethyl hexanaldehyde, iso-valeraldehyde, chloraldehyde hydrate, furfuraldehyde, paraformaldehyde.

3. The stable aqueous aldehyde solution according to claim 1 wherein the aldehyde is selected from the group consisting of: glutaraldehyde and ethane dialdehyde; ethane dialdehyde and chloraldehyde trihydrate; acetaldehyde and Glyoxal™; paraformaldehyde and glutaraldehyde, glutaraldehyde and succinaldehyde and ethane dialdehyde and succinaldehyde.

4. The stable aqueous aldehyde solution according to claim 1 which includes the surfactant or detergent in a 0.1% to 25% m/v concentration.

5. The stable aqueous aldehyde solution according to claim 1 wherein the alcohol ethoxylate surfactant includes 3 to 9 ethoxylate groups.

6. The stable aqueous aldehyde solution according to claim 1 which includes the buffer in at least a 0.05% m/v concentration.

7. The stable aqueous aldehyde solution according to claim 1 wherein the pH modifier comprises at least one component selected from the group consisting of: potassium hydroxide, sodium hydroxide, sodium phosphate and sodium bicarbonate.

8. The stable aqueous aldehyde solution according to claim 7 wherein the pH modifier is potassium hydroxide in a one molar solution.

9. The stable aqueous aldehyde solution according to claim 1 which includes a twin chain quaternary ammonium compound with sterically hindered ammonium groups.

10. The stable aqueous aldehyde solution according to claim 1 which includes one or more trace elements selected from the group consisting of: calcium, magnesium, zinc, copper, titanium, iron, silver, sodium and gold.

11. The stable aqueous aldehyde solution according to claim 10 wherein copper is included as cupric chlorate or cupric sulphate.

12. The stable aqueous aldehyde solution according to claim 11 wherein zinc is included as zinc perchlorate, zinc chloride or zinc sulphate.

13. The stable aqueous aldehyde solution according to claim 1 which includes sodium nitrite in a concentration not exceeding 0.005% m/v.

14. A biocidal dispersant which includes the stable aqueous aldehyde solution according to claim 1, diluted with distilled water.

15. The biocidal dispersant according to claim 14 which includes the aldehyde in a 0.001% to 8% m/v concentration.

* * * * *